United States Patent [19]

Purcell et al.

[11] 4,243,665
[45] Jan. 6, 1981

[54] 2-HETEROCYCLYLALKYL-6-METHOXY-NAPHTHALENES

[75] Inventors: Thomas A. Purcell, Fontenay aux Roses; Braham Shroot, Cachan; Daniel J. M. Galtier, Saint Cyr l'Ecole, all of France

[73] Assignee: Synthelabo, Paris, France

[21] Appl. No.: 962,760

[22] Filed: Nov. 21, 1978

[30] Foreign Application Priority Data

Nov. 24, 1977 [FR] France .................................. 77 35307
Oct. 16, 1978 [FR] France .................................. 78 29413

[51] Int. Cl.³ .................. C07D 241/04; C07D 275/00; A61K 31/54; A61K 31/495
[52] U.S. Cl. ............................ 424/246; 424/248.58; 424/250; 544/58.2; 544/59; 544/174; 544/383; 544/387; 544/390; 544/391; 544/398
[58] Field of Search ............. 544/390, 389, 391, 398, 544/383, 174, 59, 58.2; 424/250, 248.58, 246

[56] References Cited

U.S. PATENT DOCUMENTS

| | | | |
|---|---|---|---|
| 2,724,713 | 11/1955 | Goldman | 544/389 |
| 2,858,312 | 10/1958 | Olin | 544/398 |
| 3,239,528 | 3/1966 | Bebenburg et al. | 544/390 |
| 3,935,214 | 1/1976 | Zellner | 544/398 |
| 4,125,612 | 11/1978 | Sherlock | 544/391 |

FOREIGN PATENT DOCUMENTS

50-151885  12/1975  Japan ....................... 544/391

*Primary Examiner*—Henry R. Jiles
*Assistant Examiner*—Jane T. Fan
*Attorney, Agent, or Firm*—Stevens, Davis, Miller & Mosher

[57] ABSTRACT

Compounds corresponding to the formula

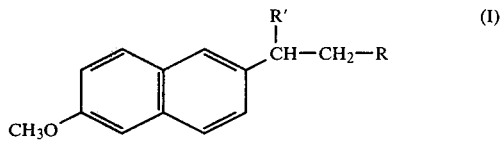

in which R' is a hydrogen atom or a methyl radical and R represents a radical

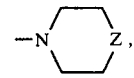

in which Z is O, S, S→O, $SO_2$ or $NR_1$, in which $R_1$ is a hydrogen atom or an alkyl, $CONR_2R_3$, $COOR_2$, $COR_2$ or $SO_2R_2$ radical, $R_2$ and $R_3$ each representing, independently of one another, a hydrogen atom, an alkyl radical having 1 to 4 carbon atoms, a phenyl radical or a $CF_3$ radical, in the form of racemates or enantiomers if R' is $CH_3$, and also, where appropriate, their addition salts with pharmaceutically acceptable acids.

The compounds and salts are useful as anti-inflammatory agents, e.g. for treatment of arthritis. A process for preparing them and pharmaceutical compositions containing them are also claimed.

7 Claims, No Drawings

2-HETEROCYCLYLALKYL-6-METHOXY-NAPHTHALENES

DESCRIPTION

The present invention relates to new naphthalene derivatives and, where appropriate, their addition salts with pharmaceutically acceptable acids; their preparation and the medicaments in which they are present as the active principle.

The invention provides a compound of the formula

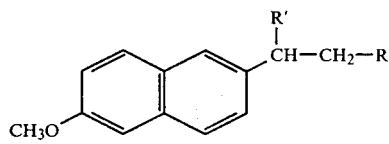

in which R' is a hydrogen atom or a methyl radical and R represents a radical

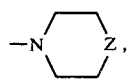

in which Z is O, S, S→O, $SO_2$ or $NR_1$, in which $R_1$ is a hydrogen atom or an alkyl, $CONR_2R_3$, $COOR_2$, $COR_2$ or $SO_2R_2$ radical, $R_2$ and $R_3$ each representing, independently of one another, a hydrogen atom, an alkyl radical having 1 to 4 carbon atoms, a phenyl radical or a $CF_3$ radical, and, where appropriate, addition salts thereof with pharmaceutically acceptable acids.

The compounds and salts in which R' is $CH_3$ possess a center of asymmetry, and their racemates and enantiomers form part of the invention.

These compounds and salts are useful in therapy in the anti-inflammatory field.

According to the invention, the compounds are prepared either by reacting the acid halide

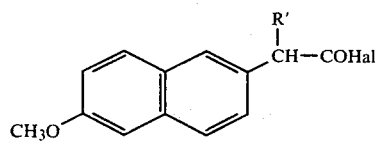

with the appropriate heterocyclic amine RH (III) in a solvent such as chloroform, at a temperature of 0° to 25° C., and then reducing the intermediate obtained (IV) in a solvent such as tetrahydrofuran, at a temperature of 0° to 80° C.; or by reacting the mesylate (V)

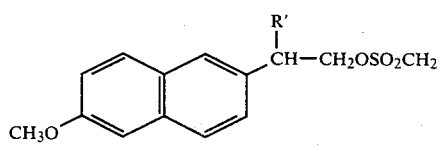

(obtained by reacting the corresponding naphthalene alcohol with a methylsulphonyl halide in a solvent such as $CH_2Cl_2$, at a temperature of 0° to 25° C.) with the amine RH in a solvent such as isopropanol, at a temperature of 25° to 150° C.

These two processes can be varied to suit the radical R, these variants being carried out in accordance with conventional methods.

The aforesaid intermediates of the formula (IV)

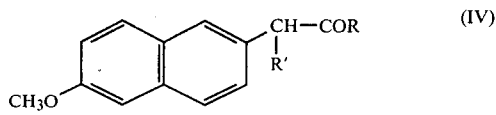

are also new.

Certain compounds (I) can be converted to other compounds (I) by conventional methods. For example, the oxidation of a compound (I) in which R is

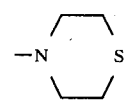

leads to the compound (I) in which R is

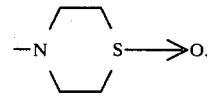

The derivatives in which R is

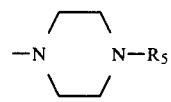

are prepared from the derivatives I in which R is

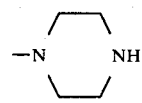

by condensation, $R_5$ being the appropriate residue for forming the N-substituted piperazino group in question (see hereinafter).

The compound of the formula (II) and the corresponding starting acid are known and described in U.S. Pat. No. 4,005,093.

The compounds in which R' is $CH_3$ are obtained in the form of enantiomers because the corresponding starting compound (II) is itself optically active.

The following reaction schemes illustrate the preparation of the compounds.

Scheme A

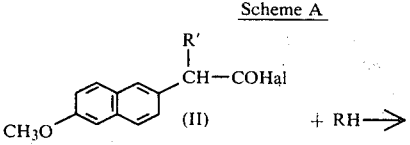

-continued

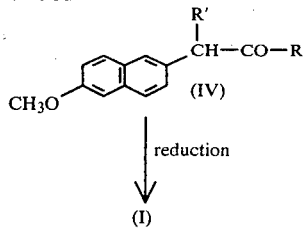

Scheme A₁

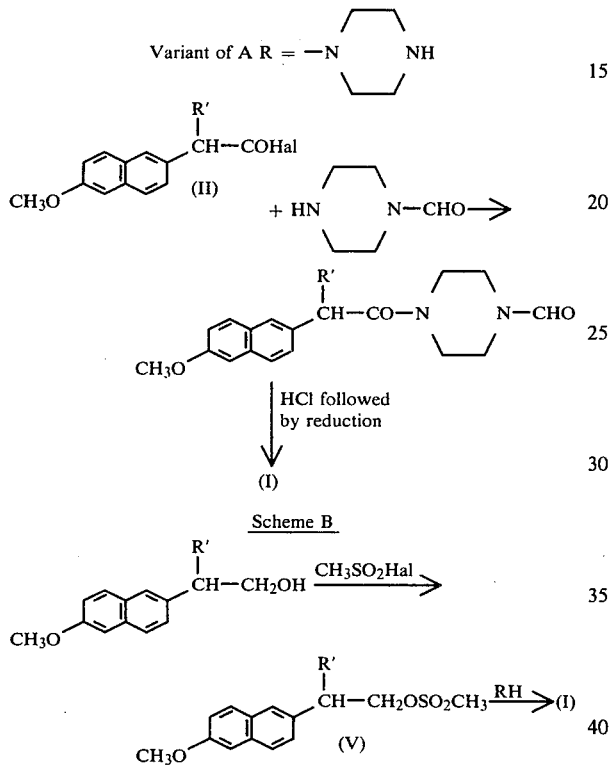

Scheme B

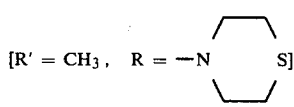

The following examples illustrate the invention. The IR and NMR spectra confirm the structure of the compounds.

EXAMPLE 1

2-[2-(Thiamorpholin-4-yl)-1-methylethyl]-6-methoxynaphthalene

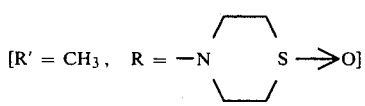

Oxalyl chloride (10 ml) is added dropwise to a suspension of 2-(6-methoxynaphth-2-yl)-propionic acid (17.4 g, 75.6 mmols) in benzene (200 ml). After refluxing for 2 hours, the benzene is evaporated off under reduced pressure and the residue is taken up in alcohol-free methylene chloride (100 ml). This solution is added dropwise, in the course of 30 minutes, to a cooled suspension (0° C.) of thiamorpholine hydrochloride (11.6 g, 83.16 mmols) and N-ethylmorpholine (19.12 g, 166 mmols) in methylene chloride (100 ml). After standing overnight, the reaction medium is washed successively with water, hydrochloric acid (10% strength), water, aqueous sodium bicarbonate solution (saturated) and water and then dried (Na₂SO₄) and evaporated. This yields a solid which is the intermediate (IV). A solution of this amide (5.60 g, 17.78 mmols) in tetrahydrofuran (50 ml) is added dropwise to a stirred solution of borane (55 mmols) in tetrahydrofuran (50 ml), which has been cooled to 0° C. The solution is then heated at the reflux temperature for 2 hours and again cooled to 0° C. Water is then added cautiously in order to destroy the excess borane, and dilute hydrochloric acid is added.

After heating for one hour at the reflux temperature in order to destroy the borane complexes, the tetrahydrofuran is then distilled under reduced pressure and the resulting aqueous suspension is partitioned between dilute sodium hydroxide solution and ethyl acetate.

The organic phase is separated off, washed with water, dried (Na₂SO₄) and evaporated. This yields a residue which crystallises from ethanol in the form of a white solid. Melting point = 88°–89° C.

EXAMPLE 2

2-[2-(1-Oxothiamorpholin-4-yl)-1-methylethyl]-6-methoxynaphthalene and its hydrochloride

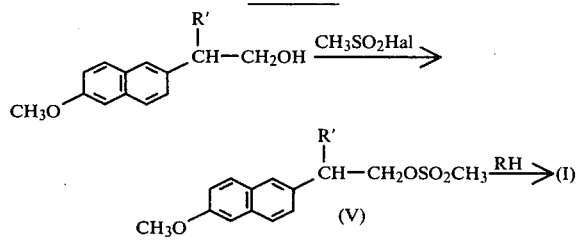

0.9 g (0.007 mol) of 30% strength hydrogen peroxide in 20 ml of acetic acid is added dropwise to 2 g (0.0067 mol) of 2-[2-(thiamorpholin-4-yl)-1-methylethyl]-6-methoxynaphthalene prepared in accordance with the method described in Example 1, which has been dissolved in 20 ml of acetic acid. The mixture is left to stand for 5 hours at ambient temperature and then heated for 4 hours at the reflux temperature. After cooling, the mixture is poured onto crushed ice and rendered alkaline with 2 N sodium hydroxide solution. The basic solution is extracted with ethyl acetate. The organic phase is washed with water and then a solution of sodium chloride and it is dried over sodium sulphate and evaporated. 1.2 g of a brown solid are collected and dissolved in 20 ml of isopropanol, and a few ml of hydrochloric acid in ether are added.

The hydrochloride which has separated out is recrystallised from isopropanol. This yields 2-[2-(1-oxothiamorpholin-4-yl)-1-methylethyl]-6-methoxynaphthalene hydrochloride which melts at 230°–231° C.

EXAMPLE 3

2-[2-(1,1-Dioxothiamorpholin-4-yl)-1-methylethyl]-6-methoxynaphthalene

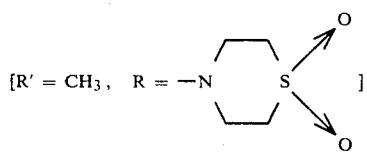

6-Methoxynaphth-2-yl-α-methylacetothiamorpholide (melting point 144°–146° C.) is prepared in accordance with the method described in Example 1. 22.9 g (0.066 mol) of this compound are suspended in 250 ml of acetic acid cooled in a waterbath. 16.5 g (0.145 mol) of 30% strength hydrogen peroxide are added dropwise.

When the addition is complete, the mixture is heated for 2 hours at the reflux temperature. After cooling, a further 5 ml of 30% strength hydrogen peroxide are added and the mixture is refluxed again for 2 hours. The mixture is left to stand overnight. The excess hydrogen peroxide is destroyed by adding a solution of sodium bisulphate in water and the solution is evaporated almost to dryness. The residue is taken up in dilute sodium bisulphate solution and ethyl acetate. The organic phase is washed with a solution of sodium carbonate, water and a solution of sodium chloride and evaporated; a light brown solid is collected and transferred rapidly onto a column of silica gel (200 g), elution being carried out with chloroform. The appropriate fractions are evaporated, combined and crystallised from ethanol to yield 11 g of 1,1-dioxo-6-methoxynaphth-2-yl-α-methylacetothiamorpholide in the form of a white solid which melts at 191°–192°. This amide is reduced by BH₃/THF in accordance with the description of Example 1.

2-[2-(1,1-Dioxothiamorpholin-4-yl)-1-methylethyl]-6-methoxynaphthalene melts at 108°–108.5° C.

EXAMPLE 4

2-(2-Piperazino-1-methylethyl)-6-methoxynaphthalene and its dihydrochloride

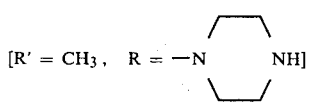

5.7 g (0.05 mol) of N-formylpiperazine are dissolved in 60 ml of methylene chloride. 6.3 ml of N-ethylmorpholine are then added and the mixture is cooled to 0°. 12.4 g (0.05 mol) of 2-(6-methoxynaphth-2-yl)-2-methylacetyl chloride in 50 ml of methylene chloride are then added dropwise to this mixture. When the addition is complete, the mixture is stirred at ambient temperature for 30 minutes. The solution is washed with water, 1 N hydrochloric acid, 8% strength sodium carbonate solution and again with water, dried over sodium sulphate and evaporated. The oily residue is stirred with ether and the mixture is placed in a refrigerator. The oil crystallises after 4 days.

The crystals are filtered off and dried and 11 g of 6-methoxynaphth-2-yl-α-methylaceto-4-formylpiperazide are collected, which melts at 108°–109° and is used immediately for the following stage.

10 g of this crude compound are dissolved in 90 ml of methanol, and 10 ml of concentrated hydrochloric acid are added at 0°. This mixture is allowed to return to ambient temperature, whilst stirring, and is kept at this temperature for 30 minutes and then heated at 40° for 5 hours.

The solvents are evaporated off and the residue is taken up in water. This aqueous solution is washed with ethyl acetate, rendered alkaline with 4 N sodium hydroxide solution and extracted with ethyl acetate. The organic phase is washed with water, dried over sodium sulphate and evaporated. The oily residue crystallises on stirring with ether. It melts at 115°–116° C.

The 6-methoxynaphth-2-yl-α-methylacetopiperazide (IV) thus obtained is used immediately for the following stage. It is reduced with a solution of borane in tetrahydrofuran (THF) (in accordance with the method described in Example 1).

When purified by chromatography on silica, elution being carried out with a mixture (98/2) of CHCl₃/(C₂H₅)₃N, and converted into the dihydrochloride in isopropanol and ether, 2-(2-piperazino-1-methylethyl)-6-methoxynaphthalene melts at 265°–270° C. (decomposition) (melting point of the salt).

EXAMPLE 5

2-[2-(4-Methylpiperazino)-1-methylethyl]-6-methoxynaphthalene

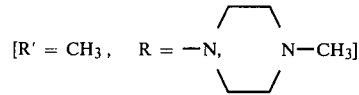

32.4 g (0.15 mol) of 2-(6-methoxynaphth-2-yl)-propan-1-ol and 20 ml of N-ethylmorpholine are dissolved in 300 ml of methylene chloride in a round-bottomed flask surrounded by an ice bath. 15 ml of methanesulphonyl chloride in 30 ml of methylene chloride are added dropwise, whilst stirring. The mixture is left to stand overnight. The solid which has precipitated is dissolved by adding 150 ml of methylene chloride and the solution is washed with water and then with a solution of sodium chloride and evaporated; 50 g of a solid are collected and washed with ether; this yields 2-(6-methoxynaphth-2-yl)-prop-2-yl methanesulphonate in the form of a whitish solid which is used without purification for the remainder of the synthesis. However, a small portion thereof was recrystallised from acetone for identification (melting point 139°–141° C.).

2.94 g (0.01 mol) of the preceding compound and 2.00 g (0.02 mol) of N-methylpiperazine in 40 ml of isopropanol are heated at the reflux temperature for 20 hours. The solution is evaporated and the residue is taken up in water and ethyl acetate. The organic layer is separated off and washed with water until the pH is 7 and then with dilute hydrochloric acid. The acid extract is separated off and washed with fresh ethyl acetate, rendered alkaline with 4 N sodium hydroxide solution and extracted with ethyl acetate. The organic phase is separated off and washed with water and then a solution of sodium chloride; it is dried over sodium sulphate and evaporated in order to collect 2-[2-(4-methylpiperazino)-1-methylethyl]-6-methoxynaphthalene.

After recrystallisation from isopropanol, the compound melts at 111°–112° C.

EXAMPLE 6

2-[2-(4-Ethoxycarbonylpiperazino)-1-methylethyl]-6-methoxynaphthalene and its hydrochloride

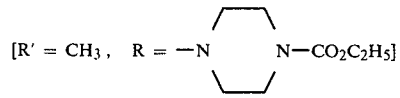

1.4 g (0.0044 mol) of the 2-(2-piperazino-1-methylethyl)-6-methoxynaphthalene dihydrochloride obtained in Example 4 are dissolved in a mixture of 20 ml of methylene chloride and 1.8 ml (0.014 mol) of N-ethylmorpholine at 0°, whilst stirring. The stirring is continued and 0.42 ml (0.0044 mol) of ethyl chloroformate is added dropwise. When the addition is complete, the mixture is stirred for a further 30 minutes, whilst keeping the temperature at 0°. The mixture is then washed with water and the organic phase is separated off, dried over sodium sulphate and evaporated. The oil obtained is taken up in ether and, by adding hydrochloric acid in ether, it is converted into its hydrochloride which, after recrystallisation from isopropanol, melts at 210°–213° C.

EXAMPLE 7

2-[2-(4-Isopropylaminocarbonylpiperazino)-1-methylethyl]-6-methoxynaphthalene and its hydrochloride

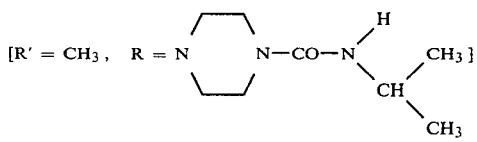

15.82 g (0.056 mol) of 2-(2-piperazino-1-methylethyl)-6-methoxynaphthalene are dissolved in 300 ml of methylene chloride and the solution is cooled using an ice bath. 6.0 ml (0.061 mol) of isopropyl isocyanate are added dropwise, whilst stirring. The reaction mixture is allowed to return to ambient temperature and left to stand overnight. The solution is then washed several times with water, dried over $Na_2SO_4$ and evaporated. The residue is crystallised from ether. Melting point = 128°–9° C.

The hydrochloride of the compound is prepared by adding hydrochloric acid in ether to a solution of the base in ethanol. The precipitate obtained is recrystallised from ethanol. Melting point = 234°–5° C.

EXAMPLE 8

2-[2-(4-Benzoylpiperazino)-1-methylethyl]-6-methoxynaphthalene

Benzoyl chloride (0.58 ml, 5 mmols) is added, at 0° C., to a solution of 2-(2-piperazino-1-methylethyl)-6-methoxynaphthalene (1.42 g, 5 mmols) and N-ethylmorpholine (0.65 ml, 5 mmols) in 15 ml of methylene chloride. The mixture is allowed to return to ambient temperature and stirred for 3 hours. The reaction medium is washed with water and dried over sodium sulphate. Concentration of the mixture yields an oily residue which dissolves in ether and crystallises. The compound is recrystallised from ethyl acetate (15 ml).

Melting point = 97° C.

The compounds which have been prepared by way of examples are shown in Table I below.

TABLE I

| Compound No. | R' | R | Melting point (°C.) |
|---|---|---|---|
| 1 | H | —N(CH₂CH₂)₂O (morpholino) | base 115–117 |
| 2 | CH₃ | —N(CH₂CH₂)₂O (morpholino) | base 118–120 |
| 3 (Example 1) | CH₃ | —N(CH₂CH₂)₂S (thiomorpholino) | base 88–89 |
| 4 (Example 2) | CH₃ | —N(CH₂CH₂)₂S→O | hydrochloride 230–231 |
| 5 (Example 3) | CH₃ | —N(CH₂CH₂)₂S(=O)₂ | base 108–108.5 |
| 6 (Example 6) | CH₃ | —N(CH₂CH₂)₂N—COO C₂H₅ | hydrochloride 210–213 |
| 7 | CH₃ | —N(CH₂CH₂)₂N—CO—NH CH₃ | base 127 |
| 8 (Example 4) | CH₃ | —N(CH₂CH₂)₂NH | dihydrochloride 265–270 (decomposition) |
| 9 (Example 5) | CH₃ | —N(CH₂CH₂)₂N—CH₃ | base 111–112 |
| 10 | CH₃ | —N(CH₂CH₂)₂N—C₆H₅ | base 187–189 |
| 11 | CH₃ | —N(CH₂CH₂)₂N—CO—NH—C₃H₇ | 144 |
| 12 (Example 7) | CH₃ | —N(CH₂CH₂)₂N—CO—NH—isoC₃H₇ | 129 |
| 13 | CH₃ | —N(CH₂CH₂)₂N—CO—N(CH₃)₂ | 114-5 |
| 14 | CH₃ | —N(CH₂CH₂)₂N—CON(H)(C₆H₅) | 152 |
| 15 | CH₃ | —N(CH₂CH₂)₂N—SO₂—C₆H₅ | 192 |
| 16 | CH₃ | —N(CH₂CH₂)₂N—SO₂—CH₃ | 153 |

TABLE I-continued

| Compound No. | R' | R | Melting point (°C.) |
|---|---|---|---|
| 17 | CH₃ | 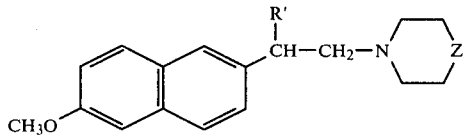 —N⟩N—CO—CH₃ | 141 |
| 18 (Example 8) | CH₃ | —N⟩N—CO—C₆H₅ | 97 |
| 19 | CH₃ | —N⟩N—CO—CF₃ | 93 |

The compounds were subjected to a series of pharmacological experiments which demonstrated their analgesic, anti-inflammatory and/or antipyretic activity.

Acute toxicity

The experiments were carried out on mice of both sexes, of the CD 1 strain, having a mean weight of 20 g.

The 50% lethal doses were calculated by a graphical method.

The majority of the compounds of the invention are of low toxicity and their LD 50 is generally more than 1,000 mg/kg, when administered orally.

Anti-inflammatory activity

This activity was determined by testing the oedema caused by carrageenin on the paws of Sherman rats, in accordance with the technique of Winter et al. (Proc. Soc. Exp. Biol. Med., 1962, 14, 544). The 40% active dose (ED 40) is determined for the compounds. It is about 15 to 200 mg/kg, when administered orally.

The compounds of the invention can be used in human and veterinary therapy, especially in the treatment of inflammatory conditions such as arthritis.

The method of administration can be oral, endorectal or parenteral.

The compounds can be produced in any pharmaceutical form which is suitable for oral, parenteral or endorectal administration, such as tablets, capsules, sugar-coated pills, suppositories, solutions which can be taken orally or injected, suspensions, ointments and the like, by themselves or in association with any suitable excipient.

The invention thus includes a pharmaceutical composition containing a compound of formula (I) or, if appropriate, a salt thereof, with a pharmaceutically acceptable acid, together with a pharmaceutically acceptable carrier or diluent.

The daily dosage can range from 200 mg to 4,000 mg. in one or more doses.

We claim:

1. A compound of the formula:

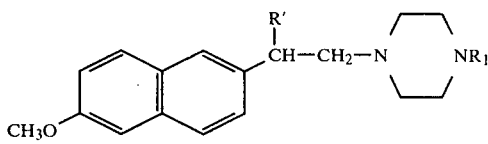

wherein
R' is hydrogen or methyl;
Z is O, S, S→O, SO₂ or NR₁;
R₁ is hydrogen, alkyl, CONR₂R₃, COOR₂, COR₂ or SO₂R₃;
each of R₂ and R₃ is independently hydrogen, alkyl, phenyl or CF₃; wherein each alkyl has 1 to 4 carbon atoms; in the form of racemate or enantiomer when R' is CH₃, or a pharmaceutically acceptable salt thereof.

2. A compound or salt according to claim 1, wherein R' is CH₃.

3. 2-[2-(1,1-Dioxothiamorpholin-4-yl)-1-methylethyl]-6-methoxynaphthalene.

4. 2-[2-(4-Isopropylaminocarbonylpiperazino)-1-methylethyl]-6-methoxynaphthalene or its hydrochloride.

5. A compound of claim 1 of the formula:

$$\text{CH}_3\text{O-naphthalene-CH(R')-CH}_2\text{-N(piperazine)NR}_1$$

6. A pharmaceutical composition having anti-inflammatory activity comprising a compound according to one of claims 2 to 4, 1 and 5 in an amount sufficient to provide said anti-inflammatory activity, together with a pharmaceutically acceptable carrier or diluent.

7. A method of treating a subject having an inflammatory condition comprising administering to said subject suffering therefrom a therapeutically effective dose of a compound according to one of claims 2 to 4, 1 and 5.

* * * * *